(12) United States Patent  
Aibara

(10) Patent No.: US 9,280,253 B2  
(45) Date of Patent: Mar. 8, 2016

(54) APPLICATION COORDINATING SYSTEM, APPLICATION COORDINATING METHOD, AND APPLICATION COORDINATING PROGRAM

(71) Applicant: PSC, Inc., Matsuyama-shi, Ehime (JP)

(72) Inventor: Teruo Aibara, Matsuyama (JP)

(73) Assignee: FINDEX Inc., Matsuyama-shi, Ehime (JP)

( * ) Notice: Subject to any disclaimer, the term of this patent is extended or adjusted under 35 U.S.C. 154(b) by 292 days.

(21) Appl. No.: 14/016,150

(22) Filed: Sep. 2, 2013

(65) Prior Publication Data

US 2014/0007003 A1 Jan. 2, 2014

Related U.S. Application Data

(63) Continuation-in-part of application No. PCT/JP2012/069796, filed on Aug. 3, 2012.

(30) Foreign Application Priority Data

Jun. 28, 2012 (JP) ................... 2012-144881

(51) Int. Cl.
*G06F 9/44* (2006.01)
*G06F 15/16* (2006.01)
(Continued)

(52) U.S. Cl.
CPC ............... *G06F 3/048* (2013.01); *G06F 9/445* (2013.01); *G06F 17/30581* (2013.01); *G06Q 10/06* (2013.01); *G06Q 50/22* (2013.01); *G06F 19/322* (2013.01)

(58) Field of Classification Search
CPC ....... G06F 9/445; G06F 9/4443; G06F 3/048; G06F 9/45512; G06F 9/4446; Y10S 707/99933

See application file for complete search history.

(56) References Cited

U.S. PATENT DOCUMENTS

| | | | |
|---|---|---|---|
| 7,587,670 B2* | 9/2009 | Snover | G06F 9/45512 715/234 |
| 7,987,455 B1* | 7/2011 | Senner | G06F 9/45512 715/700 |

(Continued)

FOREIGN PATENT DOCUMENTS

| | | |
|---|---|---|
| JP | 11-65795 A | 3/1999 |
| JP | 2001-14411 A | 1/2001 |

(Continued)

OTHER PUBLICATIONS

Tatum et al., CLI-mate: an interface generator for command line programs, Dec. 2011, 2 pages.*

(Continued)

*Primary Examiner* — Thuy Dao

(74) *Attorney, Agent, or Firm* — JTT Patent Services, LLC; Gerald T. Peters

(57) ABSTRACT

An application coordinating system may be provided with coordination rule storage device that stores coordination rule(s) pertaining to coordination source application(s) and coordination target application(s); item value acquirer that acquires item value(s) at coordination acquisition item(s) within coordination item acquisition window(s) of coordination source application(s) displayed at display device(s) during coordination; coordinated launch command generator that generates coordinated launch command(s) which include, as launch parameter(s), item value(s) acquired by item value acquirer based on coordinated launch command format(s) during coordination; and coordinated transfer protocol generator that generates coordinated transfer protocol(s) which include, as transferred data, item value(s) acquired by item value acquirer based on coordinated transfer protocol format(s) during coordination.

22 Claims, 11 Drawing Sheets

(51) Int. Cl.
*G06F 3/048* (2013.01)
*G06Q 10/06* (2012.01)
*G06Q 50/22* (2012.01)
*G06F 9/445* (2006.01)
*G06F 17/30* (2006.01)
*G06F 19/00* (2011.01)

(56) References Cited

U.S. PATENT DOCUMENTS

| | | | | |
|---|---|---|---|---|
| 8,782,647 | B2* | 7/2014 | Kajita | G06F 9/45512 709/201 |
| 8,910,063 | B2* | 12/2014 | Sarbin | G06F 3/0488 715/763 |
| 2008/0215977 | A1* | 9/2008 | Bauchot | G06F 9/4446 715/710 |
| 2011/0067025 | A1* | 3/2011 | Cragun | G06F 9/45512 718/100 |
| 2012/0192096 | A1* | 7/2012 | Bowman | G06F 3/0481 715/780 |

FOREIGN PATENT DOCUMENTS

| | | |
|---|---|---|
| JP | 2004-38759 A | 2/2004 |
| JP | 2006-190008 A | 7/2006 |
| JP | 2011-81537 A | 4/2011 |

OTHER PUBLICATIONS

IBM Corp., IBM Sterling Connect:Enterprise Command Line Client, 2011, 70 pages.*

International Search Report (ISR) in International Application (IA) No. PCT/JP2012/069796 filed Aug. 3, 2012 (published as WO/2014/002293 A1 on Jan. 3, 2014), of which the present application is a bypass continuation-in-part.

International Preliminary Report on Patentability (IPRP) with Written Opinion (WrOp) in IA No. PCT/JP2012/069796 filed Aug. 3, 2012 (published as WO/2014/002293 A1 on Jan. 3, 2014), of which the present application is a bypass continuation-in-part.

* cited by examiner

| | COORDINATION SOURCE APPLICATION | | APPLICATION A |
|---|---|---|---|
| COORDINATION SOURCE SETTINGS | ITEM ACQUISITION WINDOW | | ... |
| | ACQUISITION ITEM | PATIENT NUMBER | ... (HANDLE) |
| | | NAME | ... (HANDLE) |
| | | PHONETIC SPELLING | ... (HANDLE) |
| | | ADDRESS | ... (HANDLE) |
| COORDINATION TARGET APPLICATION SETTINGS 1 | COORDINATION TARGET APPLICATION | | APPLICATION B |
| | COORDINATED LAUNCH SETTINGS | COORDINATED LAUNCH COMMAND FORMAT | ... |
| | COORDINATED TRANSFER SETTINGS | COORDINATED TRANSFER PROTOCOL FORMAT | ... |
| | COORDINATION MODE | | COORDINATED LAUNCH |
| COORDINATION TARGET APPLICATION SETTINGS 2 | COORDINATION TARGET APPLICATION NAME | | APPLICATION C |
| | COORDINATED LAUNCH SETTINGS | COORDINATED LAUNCH COMMAND FORMAT | ... |
| | COORDINATED TRANSFER SETTINGS | COORDINATED TRANSFER PROTOCOL FORMAT | ... |
| | COORDINATION MODE | | COORDINATED TRANSFER |

FIG. 2

| LAUNCH SOURCE APPLICATION SETTINGS | |
|---|---|
| AUTOMATICALLY SEARCH FOR ACTIVE SCREEN SETTINGS | DISPLAY LIST OF LAUNCH SOURCE APPLICATION SCREENS |

SETTINGS HINTS:

LAUNCH SOURCE APPLICATION INFORMATION

| APPLICATION NAME | SELECT | MEDICAL CARE SYSTEM (RESIDENTIAL SERVICE) |
|---|---|---|
| SCREEN NAME | SELECT | PATIENT INFORMATION BASIC (1) |

PATIENT BASIC INFORMATION

| PATIENT NUMBER | SELECT | 0000140025 |
|---|---|---|
| NAME | SELECT | HANAKO MATSUYAMA |
| PHONETIC SPELLING | SELECT | HANAKO MATSUYAMA |
| SEX | SELECT | |
| DATE OF BIRTH | SET DATE FORMAT | 15 OCTOBER 1980 |

OTHER PATIENT INFORMATION

| POSTAL CODE | SELECT | 20121010 |
|---|---|---|
| ADDRESS 1 | SELECT | 4-9-6 SANBAN-CHO, MATSUYAMA-SHI, EHIME-KEN |
| ADDRESS 2 | SELECT | NBF MATSUYAMA NICHIGINMAE BUILDING 11F |
| TELEPHONE | SELECT | 089-947-33888 |
| PARAMETER 1 | SELECT | |
| PARAMETER 2 | SELECT | |
| PARAMETER 3 | SELECT | |

| CLEAR SCREEN | | SAVE SETTINGS | CLOSE |
|---|---|---|---|

APPLICATION COORDINATING SYSTEM, APPLICATION COORDINATING METHOD, AND APPLICATION COORDINATING PROGRAM

CROSS-REFERENCE TO RELATED APPLICATION, PRIORITY CLAIMS, AND INCORPORATION BY REFERENCE

This application is a continuation-in-part of and claims benefit under 35 USC 120 and 365(c) to International Application No PCT/JP2012/069796, entitled "Application Coordinating System, Application Coordinating Method, and Application Coordinating Program", filed 3 Aug. 2012; and further claims benefit of priority under 35 USC 119(a)-(d) to Japanese Patent Application No 2012-144881, entitled "Application Coordinating System, Application Coordinating Method, and Application Coordinating Program", filed 28 Jun. 2012, the contents of both of which applications are incorporated herein in their entireties by reference.

FIELD OF THE INVENTION

The present invention relates to an application coordinating system for carrying out processing with coordination between or among applications.

BACKGROUND

Coordinating systems for carrying out coordination between or among applications have been provided conventionally. For example, in one such system, coordination of data among a plurality of applications is carried out by means of a service portal having a plurality of windows displaying processing results from a plurality of applications.

However, with conventional application coordinating systems, it has been the case that the rules for achieving coordination between or among the applications that are to be coordinated have been established in advance, with special-purpose coordination systems being developed thereafter, and so enormous effort and expense have been required for coordination of the master data which is shared between or among applications and for transfer of data for update thereof. Furthermore, there has been poor universality, it being the case that change(s) to coordination target and/or coordination source application(s) have necessitated that the system be rebuilt from scratch.

The present invention was conceived in light of such problems, it being an object thereof to provide an application coordinating system that is inexpensive and is highly universal.

SUMMARY OF INVENTION

In order to solve the aforesaid problems, an application coordinating system associated with one embodiment of the present invention may be provided with an arithmetic unit, a storage device, and a display device.

The application coordinating system may carry out coordination between a coordination source application that manages a plurality of records and a coordination target application.

The storage device may have a coordination rule storage unit that stores at least one coordination rule.

The at least one coordination rule may include information pertaining to the coordination source application, a coordination item acquisition window, a coordination acquisition item, a coordination target application, and a coordinated launch command format.

The coordination item acquisition window may be a record display window of the coordination source application and may be such that an item value is acquired therefrom during coordination.

The coordination acquisition item may be an item displayed within said coordination item acquisition window and may be such that an item value is acquired therefrom during coordination.

The coordinated launch command format may cause the coordination target application to be launched in coordinated fashion with respect to the coordination source application.

The application coordinating system may be provided with an item value acquirer. The item value acquirer may acquire the item value of the coordination acquisition item within the coordination item acquisition window displayed at the display device during coordination.

The application coordinating system may be provided with a coordinated launch command generator. The coordinated launch command generator may generate a coordinated launch command. The coordinated launch command may include as launch parameter the item value acquired by the item value acquirer based on the coordinated launch command format during coordination.

Execution of the coordinated launch command may cause execution of coordinated launch such that the coordination target application is launched with the item value acquired by the item value acquirer serving as the launch parameter therefore during coordination.

An application coordinating program associated with another embodiment of the present invention may cause a computer to carry out processing causing coordination between a coordination source application that manages a plurality of records and a coordination target application. The computer may be provided with an arithmetic unit, a storage device, and a display device.

The application coordinating program may cause the computer to execute a coordination rule storage step, an item value acquisition step, a coordinated launch command generation step, and a coordinated launch step.

The coordination rule storage step may be such that at least one coordination rule is stored at the storage device.

The at least one coordination rule may include information pertaining to the coordination source application, a coordination item acquisition window, a coordination acquisition item, a coordination target application, and a coordinated launch command format.

The coordination item acquisition window may be a record display window of the coordination source application and may be such that an item value is acquired therefrom during coordination.

The coordination acquisition item may be an item displayed within said coordination item acquisition window and may be such that an item value is acquired therefrom during coordination.

The coordinated launch command format may cause the coordination target application to be launched in coordinated fashion with respect to the coordination source application.

The item value acquisition step may be such that the item value of the coordination acquisition item within the coordination item acquisition window displayed at the display device is acquired during coordination.

The coordinated launch command generation step may be such that a coordinated launch command which includes as launch parameter the item value acquired at the item value acquisition step based on the coordinated launch command format is generated during coordination.

The coordinated launch step may be such that execution of the coordinated launch command causes the coordination target application to be launched with the item value acquired at the item value acquisition step serving as the launch parameter therefore during coordination.

An application coordinating method associated with yet another embodiment of the present invention may carry out coordination between a coordination source application that manages a plurality of records and a coordination target application.

The application coordinating method may be carried out using a computer. The computer may be provided with an arithmetic unit, a storage device, and a display device.

The application coordinating method may comprise a coordination rule storage step, an item value acquisition step, a coordinated launch command generation step, and a coordinated launch step.

The coordination rule storage step may be such that at least one coordination rule is stored at the storage device.

The at least one coordination rule may include information pertaining to the coordination source application, a coordination item acquisition window, a coordination acquisition item, a coordination target application, and a coordinated launch command format.

The coordination item acquisition window may be a record display window of the coordination source application and may be such that an item value is acquired therefrom during coordination.

The coordination acquisition item may be an item displayed within said coordination item acquisition window and may be such that an item value is acquired therefrom during coordination.

The coordinated launch command format may cause the coordination target application to be launched in coordinated fashion with respect to the coordination source application.

The item value acquisition step may be such that the arithmetic unit acquires the item value of the coordination acquisition item within the coordination item acquisition window displayed at the display device during coordination.

The coordinated launch command generation step may be such that the arithmetic unit generates a coordinated launch command which includes as launch parameter the item value acquired at the item value acquisition step based on the coordinated launch command format during coordination.

The coordinated launch step may be such that execution of the coordinated launch command by the arithmetic unit causes the coordination target application to be launched with the item value acquired at the item value acquisition step serving as the launch parameter therefore during coordination.

In accordance with the present invention, by acquiring item value(s) at coordination acquisition item(s) within coordination item acquisition window(s) of coordination source application(s) displayed at display device(s) during coordination, and generating coordinated launch command(s) for launching coordination target application(s) which include said item value(s) as launch parameter(s), it is possible to launch coordination target application(s) with specific conditions for item(s) at coordination target(s), and to achieve inexpensive and highly universal coordination of applications.

Furthermore, in accordance with the present invention, by acquiring item value(s) at coordination acquisition item(s) within coordination item acquisition window(s) of coordination source application(s) displayed at display device(s), and generating coordinated transfer protocol(s) which include said item value(s) as transferred data, it is possible to achieve inexpensive and highly universal coordination of applications with regard to synchronization and/or transfer of data shared between or among applications.

Other embodiments, systems, methods, and features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 2 is a drawing showing constitution of coordination rules associated with an embodiment of the present invention.

FIG. 6 is a drawing showing a coordination source application settings screen for an application coordinating program associated with an embodiment of the present invention.

FIG. 7 is a drawing showing a display screen at a coordination source application during specification of settings at a coordination rule associated with an embodiment of the present invention.

DETAILED DESCRIPTION

Figure 1:
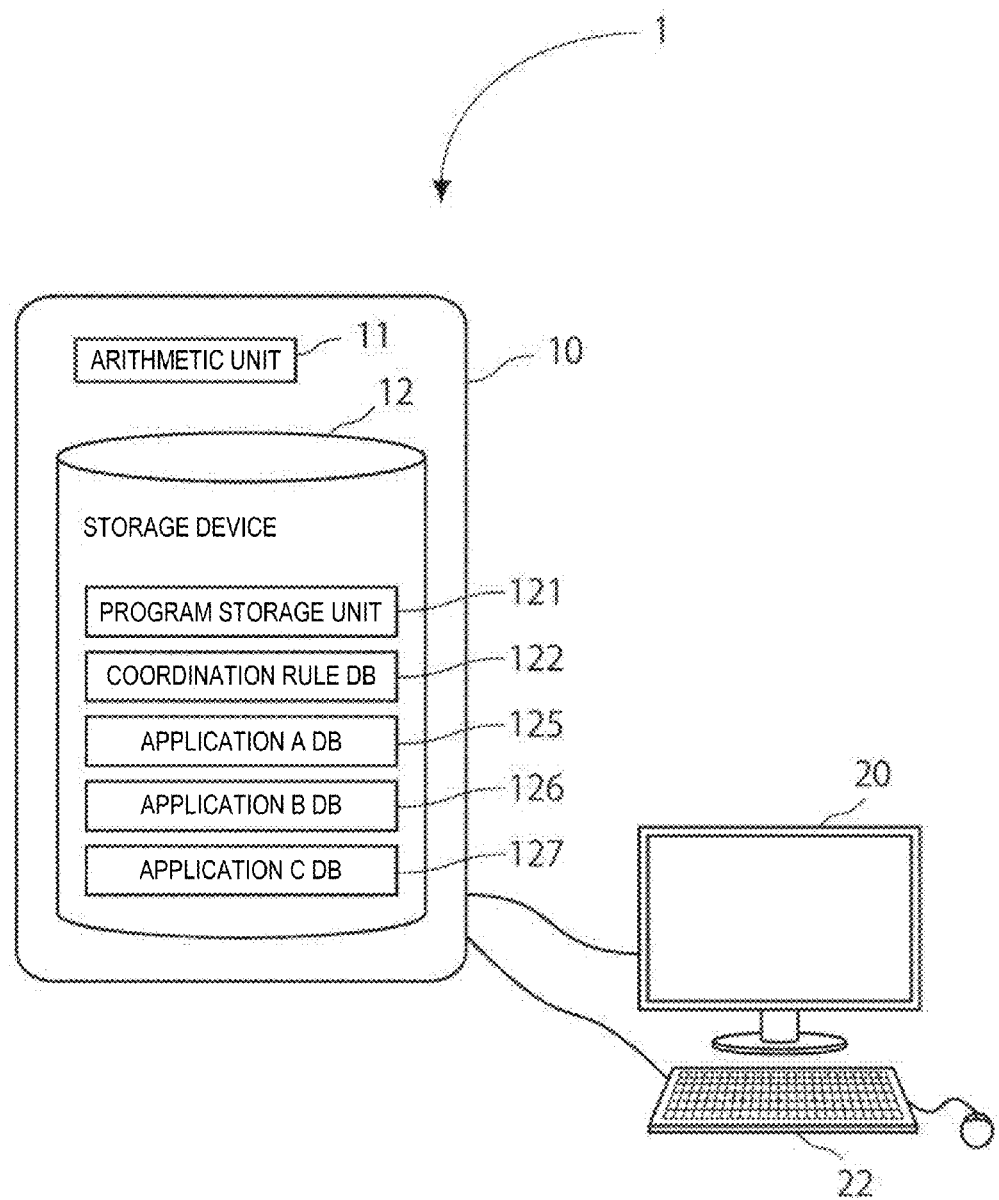
FIG. 1 is a schematic diagram showing in simplified fashion the constitution of an application coordinating system associated with an embodiment of the present invention.

An application coordinating system, which is an embodiment of the present invention, will be described in detail hereinbelow with reference to the drawings. FIG. 1 is a schematic diagram showing in simplified fashion the constitution of an application coordinating system associated with the present embodiment. FIG. 2 is a drawing showing constitution of coordination rules associated with the present embodiment.

As shown in FIG. 1, application coordinating system 1 associated with the present embodiment is provided with computer body 10, display 20 which is a display device that displays information output from computer body 10, and input device 22 comprising a keyboard, mouse, and/or the like for causing information to be input to computer body 10.

Note that the present embodiment will be described in terms of an example of a coordinating system causing coordination of medical applications A through C. Furthermore, description of the present embodiment is given in terms of a case in which applications A through C are applications for managing medical chart information, diagnostic image information, and other such patient records; application A being a coordination source application, and applications B and C being coordination target applications.

Computer body 10 is equipped with central processing unit(s) (CPU) or other such arithmetic unit(s) 11 for carrying out various types of operations, as well as storage device(s) 12 which may include hard disc drive(s) (HDD) for storing various types of information and/or random access memory or memories (RAM) capable of being used as work area(s) during arithmetic processing.

Storage device 12 is provided with program storage unit 121 for storing application coordinating program(s), applications A through C or other such executable program(s) or the like, and/or various programs for carrying out execution of prescribed processing; coordination rule database 122 for storing coordination rule(s) which are rules that have been set for carrying out execution of coordination processing between or among applications; application A database 125 for storing records managed by application A; application B database 126 for storing records managed by application B; and application C database 127 for storing records managed by application C.

An exemplary data structure for coordination rules stored at coordination rule database 122 will be described with reference to FIG. 2. As shown in FIG. 2, broadly speaking, coordination rules comprise settings information related to coordination source application(s) and settings information related to coordination target application(s). In the present embodiment, application A is a coordination source application, and applications B and C are coordination target applications.

Registered as coordination rule(s) pertaining to coordination source application(s) are the name(s) of the coordination source application(s), the name(s) of the item acquisition window(s), the item name(s) of acquisition item(s), and information indicating position(s) of respective acquisition item(s) within the item acquisition window(s).

An item acquisition window is a record display window at a coordination source application which is such that item values (objects) are acquired therefrom during coordination. Acquisition items are items which are displayed within the item acquisition window and which are such that item values are acquired therefrom during coordination.

Because in one embodiment the positions of respective items within the item acquisition window must be known if item values are to be acquired therefrom, sets of names of acquisition items together with position information therefore are registered as sets at the coordination rule. In the present embodiment, position information for acquisition items is registered in the form of window handle values.

Furthermore, registered as coordination rule settings pertaining to coordination target application(s) are the name(s) of the coordination target application(s); coordinated launch settings, in the form of format(s) of coordinated launch command(s) (coordinated launch command format(s)), for causing coordinated launch of the coordination target application(s) in question; coordinated transfer settings, in the form of format(s) of coordinated transfer protocol(s) (coordinated transfer protocol format(s)), for transferring coordination data to the coordination target application(s) in question; and coordination mode(s).

A coordinated launch command is a command for causing coordinated launch of coordination target application(s) with specific conditions for item(s) at coordination target(s) while causing item values acquired from coordination source application(s) to be passed to coordination target application(s); for example, "(full path)application A.exe -n patient_number" might be registered as a setting. By thus causing patient number(s) acquired from coordination source application(s) to be set as launch parameter(s) for coordination target application(s), it will be possible to achieve a situation whereby launch of coordination target application(s) causes coordinated launch such that record(s) for the same patient number(s) as record(s) which is/are displayed at coordination source application(s) will be displayed at coordination target application(s).

A coordinated transfer protocol, which is a protocol for causing item value(s) acquired from coordination source application(s) to be passed as transferred data to coordination target application(s), may be constituted so as to conform to transfer method(s), data format(s), item name(s) as defined by tag(s), and order(s) of item(s) in correspondence to data receiving conditions for coordination target application(s). Although transfer method(s), data format(s), item name(s) as defined by tag(s), and order(s) of item(s) have been mentioned by way of example, any suitable subset thereof or variation thereon may alternatively or additionally be employed. For example, in one embodiment, a coordinated transfer protocol might be such as will cause item name(s) as defined by tag(s) and item order during transfer of data from a coordination source application to match requirements for error-free receipt of such data by a coordination target application.

Execution of such a coordinated transfer protocol makes it possible to achieve coordinated transfer (new registration and/or synchronization) such that item value(s) acquired from coordination source application(s), upon being received by coordination target application(s), can be stored as record(s) by coordination target application(s) without the need for any special further handling or modification.

The coordination mode setting specifies whether the aforementioned coordinated launch or the aforementioned coordinated transfer is to be carried out during coordination. Coordination rules stored at coordination rule database 122 may of course be rewritten as appropriate, and coordination mode settings may of course be changed on an as-needed basis. Note that a coordination target application may be such that only either coordinated launch or coordinated transfer is carried out during coordination, in which case only either coordinated launch settings or coordinated transfer settings need be set at the coordination rule(s). Furthermore, instead of the application name and/or the window name, any other suitable identifier(s) permitting identification thereof may be registered at the coordination rule(s).

Methods for specifying settings at the aforesaid coordination rules will now be described with reference to FIG. 3 through FIG. 7.

Figure 3:
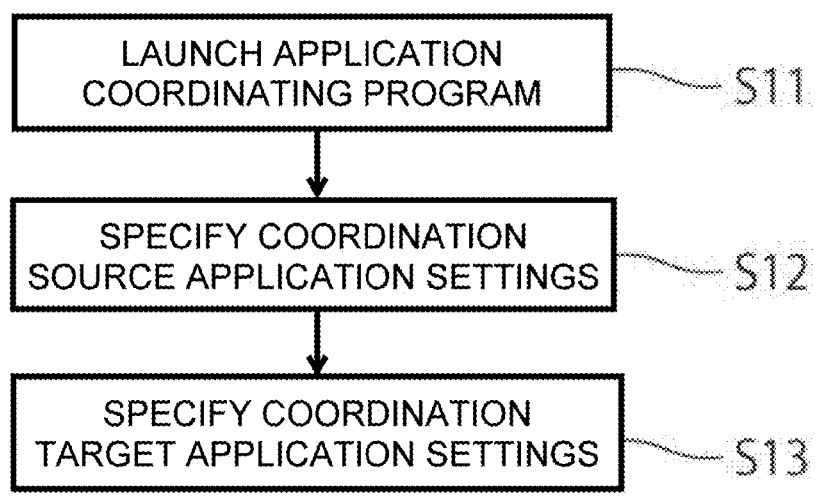
FIG. 3 is a flowchart showing a procedure for specifying settings at coordination rules associated with an embodiment of the present invention.
Figure 4:
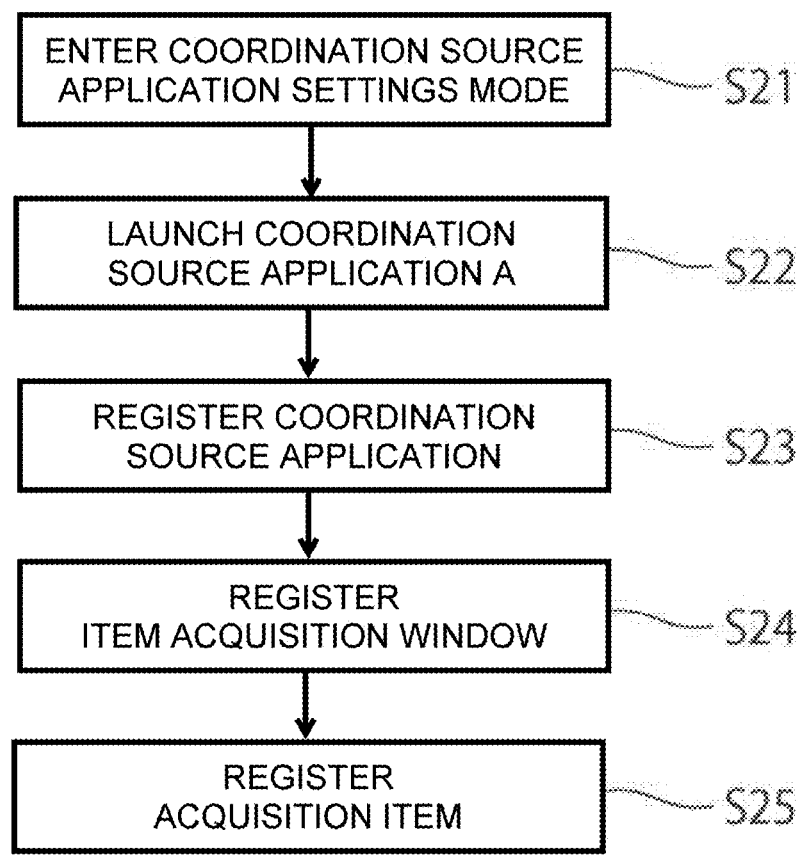
FIG. 4 is a flowchart showing a procedure for specifying settings pertaining to a coordination source application at a coordination rule associated with an embodiment of the present invention.
Figure 5:
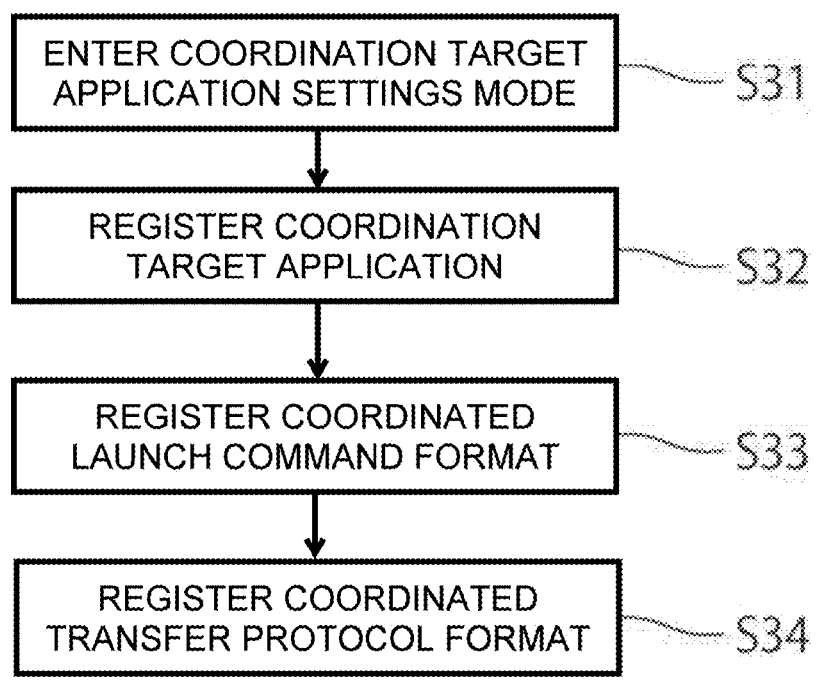
FIG. 5 is a flowchart showing a procedure for specifying settings pertaining to a coordination target application at a coordination rule associated with an embodiment of the present invention.

FIG. 3 is a flowchart showing a procedure for specifying settings at coordination rules associated with the present embodiment. FIG. 4 is a flowchart showing a procedure for specifying settings pertaining to a coordination source application at a coordination rule associated with the present embodiment. FIG. 5 is a flowchart showing a procedure for specifying settings pertaining to a coordination target application at a coordination rule associated with the present embodiment.

Figure 7:
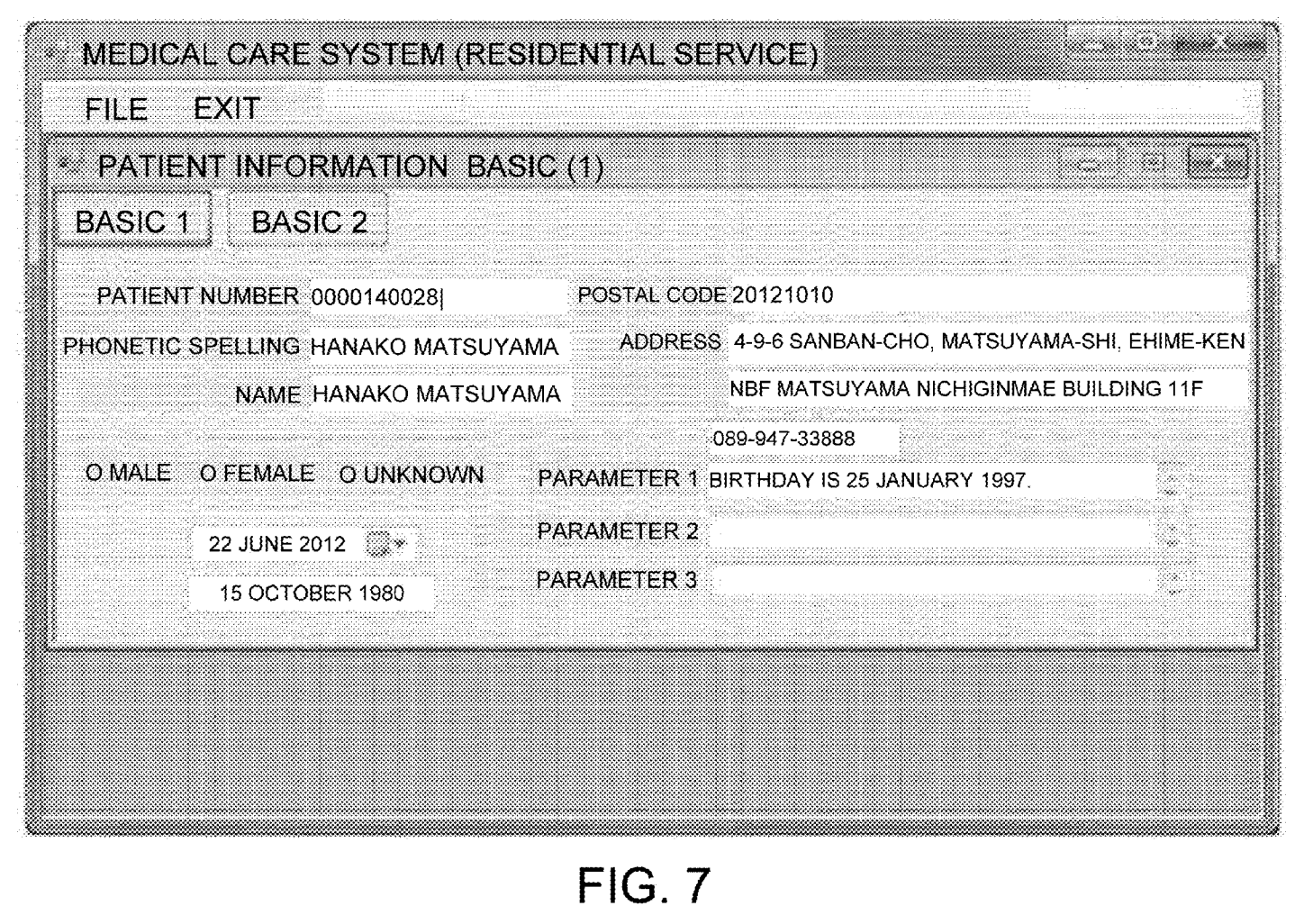

FIG. 6 is a drawing showing a coordination source application settings screen for an application coordinating program associated with the present embodiment. FIG. 7 is a drawing showing a display screen at a coordination source application during specification of settings at a coordination rule associated with the present embodiment. In the present embodiment, note that specification of coordination source application settings is carried out through use of a graphical user interface (GUI) by way of screen(s) at display 20, and specification of coordination target application settings is carried out by directly editing settings file(s). Of course, specification of either type of coordination rule settings may be carried out by either or both of the two methods described by way of example here or may be carried out in any other suitable way.

As shown in FIG. 3, specification of coordination rule settings is carried out by launching an application coordinating program as indicated at S11. More specifically, arithmetic unit 11 loads an application coordinating program which is stored at program storage unit 121 and executes same.

At S12, specification of coordination rule settings related to coordination source application(s) is carried out. More specifically, as shown in FIG. 4, the application coordinating program is placed in coordination source application settings mode as indicated at 521, and the coordination source application settings screen of the application coordinating program is opened. FIG. 6 is a drawing showing a coordination source application settings screen for an application coordinating program associated with the present embodiment. Note that what is displayed as the "LAUNCH SOURCE APPLICATION" at FIG. 6 refers to the coordination source application.

Application A, which is a coordination source application, is then launched as indicated at S22. At this time, launch takes place in such manner that a record display window which displays record(s) managed by the coordination source application is displayed at display 20. Note that where application A has a plurality of record display windows, that or those record display window(s) that display item(s) desired to be coordinated during coordination is/are launched. FIG. 7 is a drawing showing a display screen at application A during specification of settings at a coordination rule associated with the present embodiment.

Thus, with the windows shown in FIG. 6 and FIG. 7 displayed at display 20, application A is set as the coordination source application as indicated at S23. This causes the name of application A to be registered in the coordination source application name field at the coordination source settings in the coordination rule stored at the aforementioned coordination rule database 122.

More specifically, after using a mouse pointer to select the SELECT button which appears beside APPLICATION NAME beneath LAUNCH SOURCE APPLICATION INFORMATION at the settings screen shown in FIG. 6, using the mouse pointer to select the frame of the window of application A (the frame displayed as MEDICAL CARE SYSTEM (RESIDENTIAL SERVICE) in FIG. 7) causes the application name of application A, which has become active, to be automatically displayed (see FIG. 6) in the field beside APPLICATION NAME at the settings screen and registered as a setting at the coordination rule.

At S24, registration is carried out with respect to an item acquisition window, which is a record display window at the coordination source application from which item values (objects) are to be acquired during coordination. This causes the name of the item acquisition window at application A to be registered in the item acquisition window name field at the coordination source settings in the coordination rule stored at coordination rule database 122.

More specifically, after using a mouse pointer to select the SELECT button which appears beside SCREEN NAME beneath LAUNCH SOURCE APPLICATION INFORMATION at the settings screen shown in FIG. 6, using the mouse pointer to select the frame of the record display window of application A (the frame displayed as PATIENT INFORMATION BASIC (1) in FIG. 7) causes the window name of the record display window in question, which has become active, to be automatically displayed (see FIG. 6) in the field beside SCREEN NAME at the settings screen and registered as a setting at the coordination rule.

At S25, setting is carried out with respect to items within the aforesaid item acquisition window that are to be acquisition item(s), for which item value(s) will be acquired therefrom during coordination. This causes name(s) of item(s) selected at S25 to be registered in the acquisition item field at the coordination source settings in the coordination rule stored at coordination rule database 122.

More specifically, here, PATIENT NUMBER, NAME, PHONETIC SPELLING, SEX, and DATE OF BIRTH beneath PATIENT BASIC INFORMATION at the settings screen shown in FIG. 6, and POSTAL CODE, ADDRESS 1, ADDRESS 2, TELEPHONE, and other such items beneath OTHER PATIENT INFORMATION at same settings screen, are set as acquisition items. Of course, the item names for the acquisition items shown at the aforesaid settings screen are merely examples, it being possible for changes to be made to the content of the settings screen as appropriate.

The user carries out specification of settings by using a mouse pointer to select the SELECT buttons which appear beside the aforesaid respective items at the settings screen, and thereafter using the mouse pointer to sequentially select the display fields which display the item values that correspond to the respective items within the record display window of FIG. 7 (item acquisition window).

This causes the item names of acquisition items that are to be acquired from record(s) of the coordination source application during coordination, as well as item position information (window handles) identifying the positions of the acquisition items in question within the item acquisition window, to be sequentially registered at the acquisition item field of the coordination rule.

Moreover, during specification of settings for acquisition items, so as to be able to determine whether item value display fields within the item acquisition window are correctly selected in correspondence to respective items at the settings screen, selected item values (PATIENT NUMBER: 0000140025, NAME: HANAKO MATSUYAMA, etc.) are sequentially displayed beside the SELECT buttons at the settings screen (see FIG. 6).

Here, in the present embodiment, item acquisition during coordination is carried out using window handles, position information for acquisition items registered at the coordination rule being stored in the form of window handle values.

However, because there are also situations in which an item acquisition window for a coordination source application may not be capable of carrying out acquisition of item values using window handles, it is also possible in the present embodiment to carry out acquisition by extracting item values from hypertext markup language (HTML) data that makes up the item acquisition window, and/or to carry out acquisition of item values by performing optical character recognition (OCR) processing on acquisition item fields at the item acquisition window.

Which among window handles, HTML data, and/or OCR processing is to be employed for acquisition of item values might be set to the desired degree of specificity during specification of coordination source application settings. For example, this might be set separately for each coordination source application, for each coordination source application window, and/or for each acquisition item. In one embodiment, this might be set in correspondence to the type of item acquisition window, since different types of item acquisition windows will often lend themselves more readily to acquisition of item values by one of these three exemplary methods than by the other two.

When acquisition of item values from HTML data is to be carried out, item position information at the coordination rule is stored in the form of values of tags for respective acquisition items; and when acquisition of item values is to be carried out using OCR processing, item position information at the coordination rule is stored in the form of regions at which OCR processing is to be carried out, i.e., information indicating coordinates of regions of respective acquisition items within the item acquisition window.

At S13, specification of coordination rule settings related to coordination target application(s) is carried out. More specifically, as shown in FIG. 5, coordination target application settings mode is entered as indicated at S31. More specifically, the settings file for the coordination rule related to the coordination target application is opened in edit mode.

Whereas specification of settings for the aforementioned coordination source application was carried out via the GUI using a settings screen, specification of settings is carried out here through direct editing of settings file(s) related to coordination target application(s). For this reason, the coordination target settings file(s) opened in an editable state are the one(s) that contain settings which, of the coordination rule(s) referenced by the application coordinating program during coordination, are related to the coordination target application(s).

At S32, registration is carried out with respect to coordination target application(s). For example, registration might be carried out by causing the application name of a coordination target application and the path of a program for execution thereof to be written to a settings file.

Furthermore, at S33, the format of the coordinated launch command used when coordinated launch of that coordination target application is carried out might be registered. The coordinated launch command format might be registered by writing the command format in question to the settings file.

At S34, registration is carried out with respect to the format of the coordinated transfer protocol to be used when data acquired from the coordination source application is transferred to the coordination target application. The coordinated transfer protocol format might be registered by writing the protocol format in question to the settings file.

Specification of coordination target application settings is completed as a result of carrying out S32 through S34. Where, as in the present embodiment, specification of settings is to be carried out for a plurality of coordination target applications, S32 through S34 may be repeated as many times as necessary or desirable.

As a result of the foregoing, specification of coordination rule settings is completed.

Figure 8:
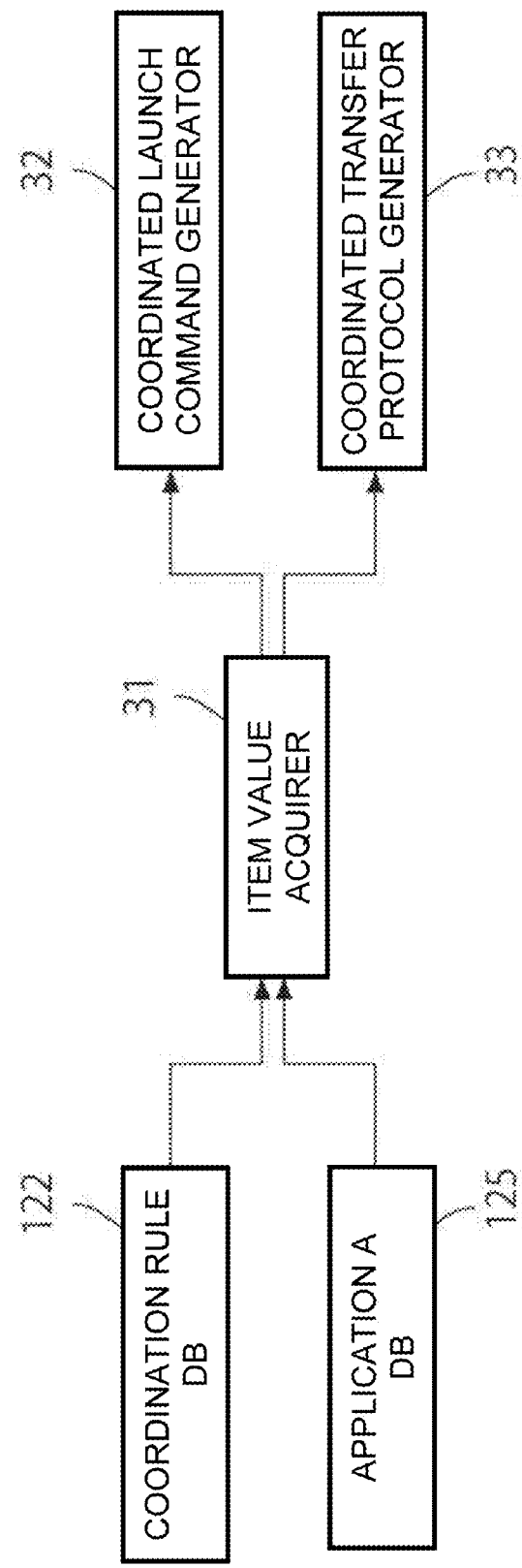
FIG. 8 is a block diagram showing in simplified fashion the functionalities at an application coordinating system associated with an embodiment of the present invention.

Functionalities of application coordinating system 1 will now be described with reference to FIG. 8. As shown in same drawing, application coordinating system 1 is provided with item value acquirer 31, coordinated launch command generator 32, and coordinated transfer protocol generator 33. These functionalities are implemented as a result of execution by arithmetic unit 11 of an application coordinating program stored at program storage unit 121.

During coordination, item value acquirer 31 acquires item value(s) of acquisition item(s) from item acquisition window(s) of coordination source application(s) displayed at display 20 based on coordination rule(s) stored at coordination rule database 122.

If a coordination source application has been launched and an item acquisition window is displayed at the screen on display 20, it will be possible to carry out this acquisition of item value(s) on as-needed basis by launching the application coordinating program.

In the present embodiment, because acquisition of item values from the record display window of the coordination source application is carried out using the window handles of the acquisition items, and/or the HTML data that makes up the record display window, and/or by performing OCR processing on acquisition items while the record display window is displayed at display 20, it is possible to easily carry out acquisition of item values without the need to modify the coordination source application.

Coordinated launch command generator 32 generates launch command(s) for coordination target application(s) which include, as launch parameter(s), item value(s) acquired by item value acquirer 31 based on coordination rule(s). For example, by employing as launch parameter(s) the patient number, which is an item value that was acquired, and an argument indicating that the record of the patient number in question is to be opened, it is possible to achieve coordinated launch such that execution of that launch command causes the coordination target application to be launched in a state in which the record of the patient number in question is opened.

For example, if the coordination source application is an application A for managing patient medical chart information, and the coordination target application is an application B for editing and managing patient diagnostic images, if when looking at medical charts of a patient—which involves the coordination source application—it is desired to cause display of diagnostic images for the patient in question, it will be possible, by causing coordinated launch to be carried out in such fashion that the patient number for that patient is transferred to the coordination target application, to easily and quickly cause diagnostic images to be displayed.

Coordinated transfer protocol generator 33 generates coordinated transfer protocol(s) which include item value(s) so as to permit transfer to coordination target application(s) of such item value(s), which were acquired by item value acquirer 31, based on coordination rule(s). A coordinated transfer protocol, which is a protocol conforming to the data receiving format of the coordination target application, makes it possible to achieve coordinated transfer whereby execution of a coordinated transfer protocol causes item value(s) acquired from coordination source application(s) to be stored as record(s) of coordination target application(s).

For example, if the coordination source application is an application A for managing patient medical chart information, and the coordination target application is an application B for editing and managing patient diagnostic images, it will be possible to achieve coordinated transfer whereby information pertaining to a patient at application A is newly registered at application B, or patient information at application B is changed so as to be synchronized to reflect a change in address or the like of a patient at application A.

Flow of application coordination processing will now be described with reference to FIG. 9 through FIG. 11.

Figure 9:
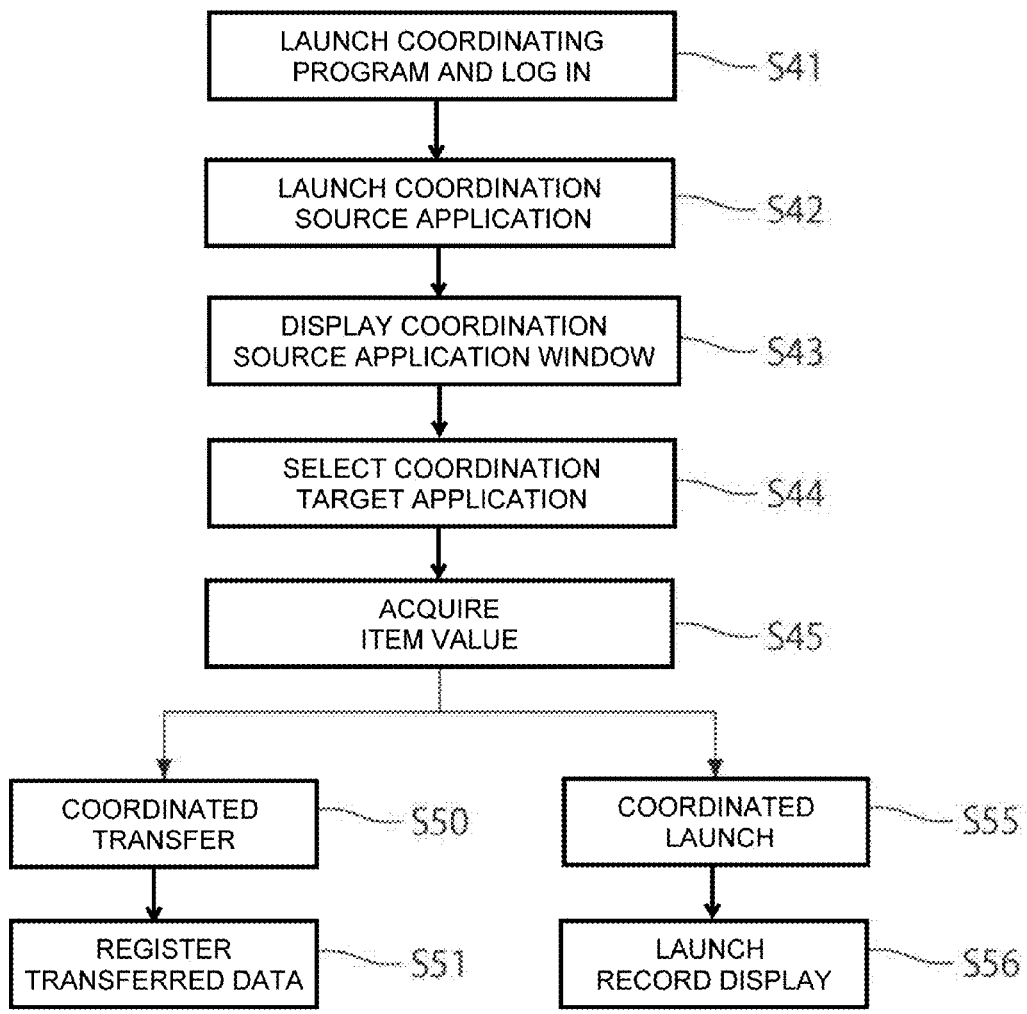
FIG. 9 is a flowchart showing flow of application coordination processing associated with an embodiment of the present invention.

FIG. 9 is a flowchart showing flow of application coordination processing associated with the present embodiment. FIG. 10 is a drawing showing a screen displayed by an application coordinating program during application coordination associated with the present embodiment. FIG. 11 is a drawing showing a screen displayed by a coordination target application during application coordination associated with the present embodiment.

At S41, a user launches an application coordinating program and logs in. Here, if the login ID and password for the application coordinating program are made to be the same as the login ID and password for coordination target application(s), by causing the login ID and password acquired during login to be included as coordinated launch command launch parameters, it will be possible to omit login entry when coordination target application(s) are launched.

Figure 10:
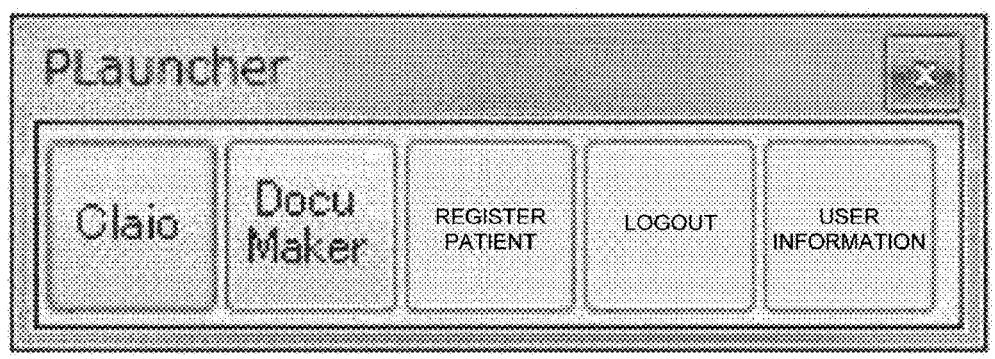
FIG. 10 is a drawing showing a screen displayed by an application coordinating program during application coordination associated with an embodiment of the present invention.
Figure 11:
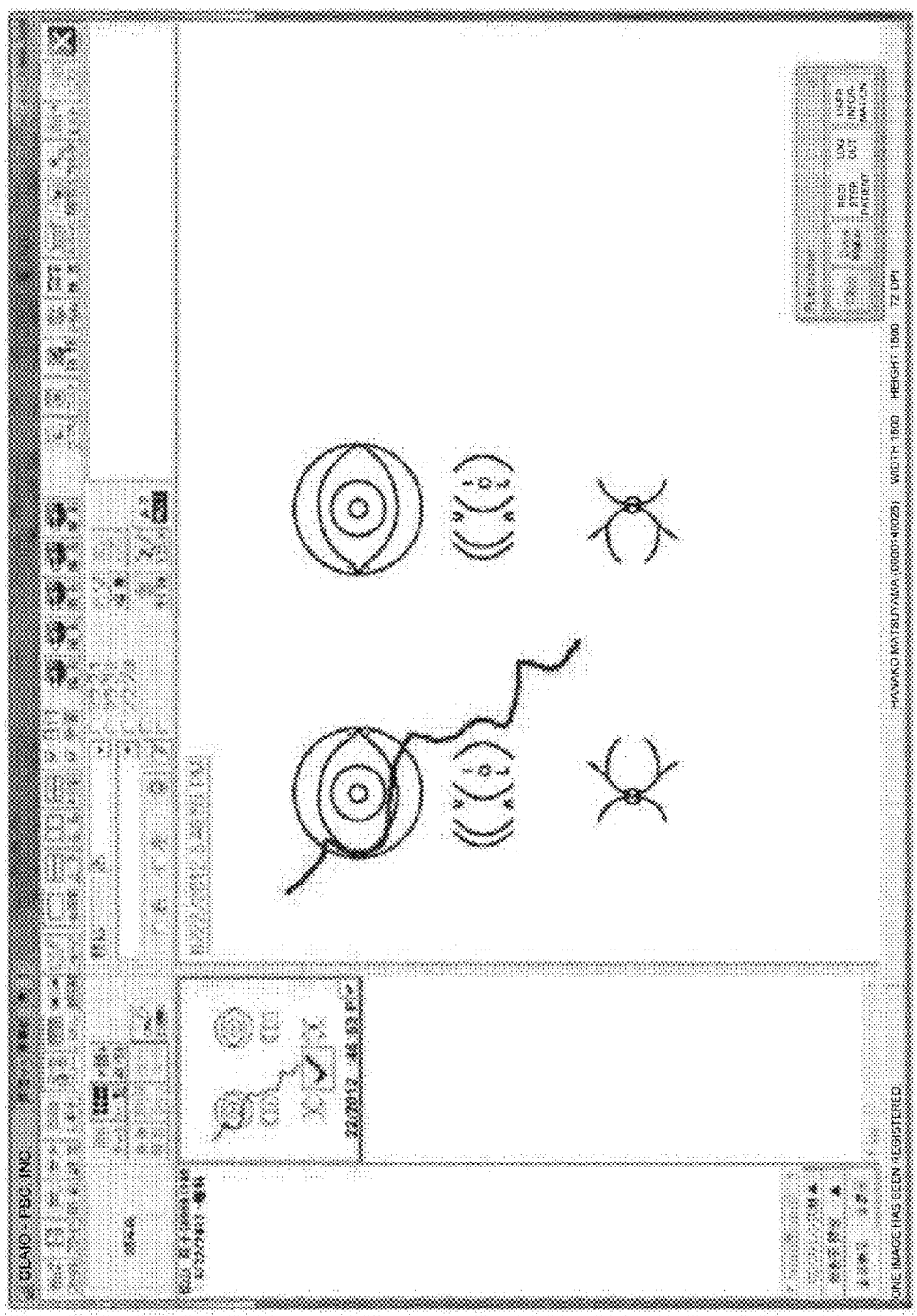
FIG. 11 is a drawing showing a screen displayed by a coordination target application during application coordination associated with an embodiment of the present invention.

When the application coordinating program is launched, the launcher shown in FIG. 10 is launched at display 20. The buttons (the CLAIO, DOCUMAKER, and other buttons at FIG. 10) displayed at the launcher include coordination buttons which serve as coordination triggers.

At S42, coordination source application(s) is/are launched; and at S43, item acquisition window(s) for which item value(s) are to be acquired during coordination is/are displayed. At this time, record(s) for which it is desired that coordination be carried out with respect to coordination target application(s) is/are displayed at item acquisition window(s).

At S44, the user selects coordination target application(s) by clicking on button(s) displayed at the launcher in FIG. 10. Selecting a coordination target application causes coordination processing to be carried out at S45 and following steps.

At S45, reference is made to those coordination rule(s) among the coordination rule(s) stored within coordination rule database 122 for which the coordination source application(s) launched at S42 are registered as coordination source(s), and acquisition of item value(s) by item value acquirer 31 is carried out.

Following S45, reference is made to coordination rule(s), and coordinated transfer is carried out at S50, and/or coordinated launch is carried out at S55, in accordance with coordination mode setting(s) for the coordination target application(s) selected at S44. If the coordination mode is set to coordinated transfer then processing proceeds to S50, where coordinated transfer protocol generator 33 generates coordinated transfer protocol(s), and coordinated transfer is executed in such fashion that item value(s) acquired from coordination source application(s) at S45 is/are transferred to coordination target application(s). In addition, at S51, registration of transferred data in the form of coordination target application record(s) is carried out.

Furthermore, if the coordination mode is set to coordinated launch then processing proceeds to S55, where coordinated launch command generator 32 generates coordinated launch command(s), and coordinated launch of coordination target application(s) takes place with item value(s) acquired from coordination source application(s) at S45 being employed as launch parameter(s). Furthermore, at S56, a coordination target application might, for example, be launched in such fashion as to display a record that has the same identifier (patient number, etc.) as a record which is or was displayed by a coordination source application.

The present embodiment having been described in detail above, a coordinating system associated with the present embodiment, by causing coordination of coordination target application(s) while record display window(s) of coordination source application(s) is/are displayed at display 20, makes it possible to easily achieve coordinated launch and/or coordinated transfer without the need to do anything special at coordination source application(s) or coordination target application(s).

While embodiments of the present invention have been described above, modes of carrying out the present invention are not limited to the foregoing embodiments, a great many further variations being possible without departing from the gist of the present invention.

For example, whereas a single computer was used to implement an application coordinating system in the foregoing embodiment, this may be implemented such that there is distributed processing by a plurality of computers.

Furthermore, whereas the foregoing embodiment was described in terms of a situation in which there was one coordination source application, coordination rules for a plurality of coordination source applications may of course be registered, and the plurality of coordination source applications may be made to undergo coordination with one coordination target application or a plurality of coordination target applications. In such case, coordination rules would be stored separately for each coordination source application.

Furthermore, whereas a single record display window was registered as item acquisition window for the coordination source application in the foregoing embodiment, a plurality of windows may be registered as item acquisition windows.

Furthermore, whereas the foregoing embodiment was described in terms of a case in which coordination target application(s) were also application(s) for managing a plurality of records, coordination target application(s) may be other than record managing application(s). For example, where coordination target application(s) is/are application(s) for preparing patient insurance application(s), it will be possible to simplify preparation of application(s) through coordinated transfer of patient information from coordination source application(s).

All such modifications and variations are intended to be included herein within the scope of this disclosure and the present invention and protected by the following claims.

EXPLANATION OF REFERENCE NUMERALS

1 Application coordinating system
10 Computer body
11 Arithmetic unit
12 Storage device
121 Program storage unit
122 Coordination rule database (DB)
125 Application A database (DB)
126 Application B database (DB)
127 Application C database (DB)
20 Display
22 Input device
31 Item value acquirer
32 Coordinated launch command generator
33 Coordinated transfer protocol generator

What is claimed is:

1. An application coordinating program stored in a non-transitory computer-readable medium that causes a computer provided with an arithmetic unit, a storage device, and a display device to carry out processing causing coordination between a coordination source application that manages a plurality of records and a coordination target application, the application coordinating program causing the computer to execute:
- a coordination rule storage step in which at least one coordination rule is stored at the storage device, the at least one coordination rule including information pertaining to
  - the coordination source application,
    - a coordination item acquisition window which is a record display window of the coordination source application and which is such that an item value is acquired therefrom during coordination,
    - a coordination acquisition item which is an item displayed within said coordination item acquisition window and which is such that an item value is acquired therefrom during coordination,
  - the coordination target application, and
  - a coordinated launch command format for causing the coordination target application to be launched in coordinated fashion with respect to the coordination source application;
- an item value acquisition step in which the item value of the coordination acquisition item within the coordination item acquisition window displayed at the display device is acquired during coordination;
- a coordinated launch command generation step in which a coordinated launch command which includes as launch parameter the item value acquired at the item value acquisition step based on the coordinated launch command format is generated during coordination; and
- a coordinated launch step in which execution of the coordinated launch command causes the coordination target application to be launched with the item value acquired at the item value acquisition step serving as the launch parameter therefor during coordination;
- wherein at least one species selected from among the group consisting of window handle information, HTML data, and OCR processing is employed for acquisition of the item value of the coordination acquisition item within the coordination item acquisition window.

2. An application coordinating system for causing coordination between a coordination source application that manages a plurality of records and a coordination target application, the application coordinating system comprising:
- an arithmetic unit;
- a storage device comprising a non-transitory computer-readable medium; and
- a display device;
- wherein the storage device has a coordination rule storage unit that stores at least one coordination rule including information pertaining to
  - the coordination source application,
    - a coordination item acquisition window which is a record display window of the coordination source application and which is such that an item value is acquired therefrom during coordination,
    - a coordination acquisition item which is an item displayed within said coordination item acquisition window and which is such that an item value is acquired therefrom during coordination,
  - the coordination target application, and
  - a coordinated launch command format for causing the coordination target application to be launched in coordinated fashion with respect to the coordination source application;
- wherein the application coordinating system further comprises
  - an item value acquirer that acquires the item value of the coordination acquisition item within the coordination item acquisition window displayed at the display device during coordination; and
  - a coordinated launch command generator that generates a coordinated launch command which includes as launch parameter the item value acquired by the item value acquirer based on the coordinated launch command format during coordination;
- wherein execution of the coordinated launch command causes execution of coordinated launch such that the coordination target application is launched with the item value acquired by the item value acquirer serving as the launch parameter therefor during coordination; and
- wherein at least one species selected from among the group consisting of window handle information, HTML data, and OCR processing is employed for acquisition of the item value of the coordination acquisition item within the coordination item acquisition window.

3. An application coordinating system according to claim 2 wherein the at least one coordination rule stored at the coordination rule storage unit further includes information pertaining to a coordinated transfer protocol format for causing data to be passed in coordinated fashion from the coordination source application to the coordination target application;
- wherein the application coordinating system further comprises a coordinated transfer protocol generator that generates a coordinated transfer protocol which includes as transferred data the item value acquired by the item value acquirer based on the coordinated transfer protocol format during coordination; and
- wherein execution of the coordinated transfer protocol causes execution of coordinated transfer such that the item value acquired by the item value acquirer is passed from the coordination source application to the coordination target application during coordination.

4. An application coordinating system according to claim 3 wherein the at least one coordination rule stored at the coordination rule storage unit further includes
- settings information pertaining to a plurality of coordination target applications, and
- settings information for each of the coordination target applications separately indicating whether the coordinated launch or the coordinated transfer is to be carried out during coordination.

5. An application coordinating system according to claim 3 wherein the at least one coordinated transfer protocol is constituted such that at least one item name as defined by at least one tag and at least one item order conform to data receiving conditions for the coordination target application.

6. An application coordinating system according to claim 2 wherein the at least one coordination rule stored at the coordination rule storage unit further includes settings information pertaining to a plurality of coordination source applications,
- there being a separate one of the at least one coordination rule stored at the coordination rule storage unit for each of the coordination source applications.

7. An application coordinating system according to claim 2 wherein the at least one coordination rule stored at the coordination rule storage unit further includes, as information pertaining to the coordination acquisition item, display position information for the item value of the coordination acquisition item within the coordination item acquisition window.

8. An application coordinating system according to claim 2 wherein the at least one coordination rule stored at the coordination rule storage unit further includes settings information pertaining to a plurality of coordination item acquisition windows, settings information for each of the coordination item acquisition windows separately indicating which of the at least one species selected from among the group consisting of window handle information, HTML data, and OCR processing is to be employed for acquisition of the item value of the coordination acquisition item within the coordination item acquisition window.

9. An application coordinating method for causing coordination between a coordination source application that manages a plurality of records and a coordination target application in the context of a computer provided with an arithmetic unit, a storage device, and a display device, the application coordinating method comprising:

a coordination rule storage step in which at least one coordination rule is stored at the storage device, the at least one coordination rule including information pertaining to the coordination source application, a coordination item acquisition window which is a record display window of the coordination source application and which is such that an item value is acquired therefrom during coordination, a coordination acquisition item which is an item displayed within said coordination item acquisition window and which is such that an item value is acquired therefrom during coordination, the coordination target application, and a coordinated launch command format for causing the coordination target application to be launched in coordinated fashion with respect to the coordination source application;

an item value acquisition step in which the arithmetic unit acquires the item value of the coordination acquisition item within the coordination item acquisition window displayed at the display device during coordination;

a coordinated launch command generation step in which the arithmetic unit generates a coordinated launch command which includes as launch parameter the item value acquired at the item value acquisition step based on the coordinated launch command format during coordination; and a coordinated launch step in which execution of the coordinated launch command by the arithmetic unit causes the coordination target application to be launched with the item value acquired at the item value acquisition step serving as the launch parameter therefor during coordination;

wherein at least one species selected from among the group consisting of window handle information, HTML data, and OCR processing is employed for acquisition of the item value of the coordination acquisition item within the coordination item acquisition window.

10. An application coordinating system for causing coordination between a coordination source application that manages a plurality of records and a coordination target application, the application coordinating system comprising:

an arithmetic unit;

a storage device comprising a non-transitory computer-readable medium; and a display device;

wherein the storage device has a coordination rule storage unit that stores at least one coordination rule including information pertaining to the coordination source application, a coordination item acquisition window which is a record display window of the coordination source application and which is such that an item value is acquired therefrom during coordination, a coordination acquisition item which is an item displayed within said coordination item acquisition window and which is such that an item value is acquired therefrom during coordination, the coordination target application, and a coordinated launch command format for causing the coordination target application to be launched in coordinated fashion with respect to the coordination source application;

wherein the application coordinating system further comprises an item value acquirer that acquires the item value of the coordination acquisition item within the coordination item acquisition window displayed at the display device during coordination; and a coordinated launch command generator that generates a coordinated launch command which includes as launch parameter the item value acquired by the item value acquirer based on the coordinated launch command format during coordination;

wherein execution of the coordinated launch command causes execution of coordinated launch such that the coordination target application is launched with the item value acquired by the item value acquirer serving as the launch parameter therefor during coordination; and wherein window handle information is employed for acquisition of the item value of the coordination acquisition item within the coordination item acquisition window.

11. An application coordinating system for causing coordination between a coordination source application that manages a plurality of records and a coordination target application, the application coordinating system comprising:

an arithmetic unit;

a storage device comprising a non-transitory computer-readable medium; and a display device;

wherein the storage device has a coordination rule storage unit that stores at least one coordination rule including information pertaining to the coordination source application, a coordination item acquisition window which is a record display window of the coordination source application and which is such that an item value is acquired therefrom during coordination, a coordination acquisition item which is an item displayed within said coordination item acquisition window and which is such that an item value is acquired therefrom during coordination, the coordination target application, and a coordinated launch command format for causing the coordination target application to be launched in coordinated fashion with respect to the coordination source application;

wherein the application coordinating system further comprises an item value acquirer that acquires the item value of the coordination acquisition item within the coordination item acquisition window displayed at the display device during coordination; and a coordinated launch command generator that generates a coordinated launch command which includes as launch parameter the item value acquired by the item value acquirer based on the coordinated launch command format during coordination;

wherein execution of the coordinated launch command causes execution of coordinated launch such that the coordination target application is launched with the item value acquired by the item value acquirer serving as the launch parameter therefor during coordination; and wherein HTML data is employed for acquisition of the item value of the coordination acquisition item within the coordination item acquisition window.

12. An application coordinating system for causing coordination between a coordination source application that manages a plurality of records and a coordination target application, the application coordinating system comprising:

an arithmetic unit;

a storage device comprising a non-transitory computer-readable medium; and a display device;

wherein the storage device has a coordination rule storage unit that stores at least one coordination rule including information pertaining to the coordination source application, a coordination item acquisition window which is a record display window of the coordination source application and which is such that an item value is acquired therefrom during coordination, a coordination acquisition item which is an item displayed within said coordination item acquisition window and which is such that an item value is acquired therefrom during coordination, the coordination target application, and a coordinated launch command format for causing the coordination target application to be launched in coordinated fashion with respect to the coordination source application;

wherein the application coordinating system further comprises an item value acquirer that acquires the item value of the coordination acquisition item within the coordination item acquisition window displayed at the display device during coordination; and a coordinated launch command generator that generates a coordinated launch command which includes as launch parameter the item value acquired by the item value acquirer based on the coordinated launch command format during coordination;

wherein execution of the coordinated launch command causes execution of coordinated launch such that the coordination target application is launched with the item value acquired by the item value acquirer serving as the launch parameter therefor during coordination; and wherein OCR processing is employed for acquisition of the item value of the coordination acquisition item within the coordination item acquisition window.

13. An application coordinating system for causing coordination between a coordination source application that manages a plurality of records and a coordination target application, the application coordinating system comprising:

an arithmetic unit;

a storage device comprising a non-transitory computer-readable medium; and a display device;

wherein the storage device has a coordination rule storage unit that stores at least one coordination rule including information pertaining to the coordination source application, a coordination item acquisition window which is a record display window of the coordination source application and which is such that an item value is acquired therefrom during coordination, a coordination acquisition item which is an item displayed within said coordination item acquisition window and which is such that an item value is acquired therefrom during coordination, the coordination target application, and a coordinated launch command format for causing the coordination target application to be launched in coordinated fashion with respect to the coordination source application;

wherein the application coordinating system further comprises an item value acquirer that acquires the item value of the coordination acquisition item within the coordination item acquisition window displayed at the display device during coordination; and a coordinated launch command generator that generates a coordinated launch command which includes as launch parameter the item value acquired by the item value acquirer based on the coordinated launch command format during coordination;

wherein execution of the coordinated launch command causes execution of coordinated launch such that the coordination target application is launched with the item value acquired by the item value acquirer serving as the launch parameter therefor during coordination;

wherein the at least one coordination rule stored at the coordination rule storage unit further includes information pertaining to a coordinated transfer protocol format for causing data to be passed in coordinated fashion from the coordination source application to the coordination target application;

wherein the application coordinating system further comprises a coordinated transfer protocol generator that generates a coordinated transfer protocol which includes as transferred data the item value acquired by the item value acquirer based on the coordinated transfer protocol format during coordination; and wherein execution of the coordinated transfer protocol causes execution of coordinated transfer such that the item value acquired by the item value acquirer is passed from the coordination source application to the coordination target application during coordination.

14. An application coordinating system according to claim 13 wherein the at least one coordination rule stored at the coordination rule storage unit further includes settings information pertaining to a plurality of coordination target applications, and settings information for each of the coordination target applications separately indicating whether the coordinated launch or the coordinated transfer is to be carried out during coordination.

15. An application coordinating system according to claim 13 wherein the at least one coordinated transfer protocol is constituted such that at least one item name as defined by at least one tag and at least one item order conform to data receiving conditions for the coordination target application.

16. An application coordinating system according to claim 13 wherein the at least one coordination rule stored at the coordination rule storage unit further includes settings information pertaining to a plurality of coordination source applications, there being a separate one of the at least one coordination rule stored at the coordination rule storage unit for each of the coordination source applications.

17. An application coordinating system according to claim 13 wherein the at least one coordination rule stored at the coordination rule storage unit further includes, as information pertaining to the coordination acquisition item, display position information for the item value of the coordination acquisition item within the coordination item acquisition window.

18. An application coordinating system according to claim 13 wherein at least one species selected from among the group consisting of window handle information, HTML data, and OCR processing is employed for acquisition of the item value of the coordination acquisition item within the coordination item acquisition window.

19. An application coordinating system according to claim 18 wherein the at least one coordination rule stored at the coordination rule storage unit further includes settings information pertaining to a plurality of coordination item acquisition windows, settings information for each of the coordination item acquisition windows separately indicating which of the at least one species selected from among the group consisting of window handle information, HTML data, and OCR processing is to be employed for acquisition of the item value of the coordination acquisition item within the coordination item acquisition window.

20. An application coordinating system according to claim 13 wherein window handle information is employed for acquisition of the item value of the coordination acquisition item within the coordination item acquisition window.

21. An application coordinating system according to claim 13 wherein HTML data is employed for acquisition of the item value of the coordination acquisition item within the coordination item acquisition window.

22. An application coordinating system according to claim 13 wherein OCR processing is employed for acquisition of the item value of the coordination acquisition item within the coordination item acquisition window.

* * * * *